US006918769B2

(12) United States Patent
Rink (10) Patent No.: US 6,918,769 B2
(45) Date of Patent: Jul. 19, 2005

(54) VIDEO GAME FOR ASSISTING HEALING OF THE HUMAN BODY

(76) Inventor: Philip A. Rink, 250 Durr Rd., Camano Island, WA (US) 98282

( * ) Notice: Subject to any disclaimer, the term of this patent is extended or adjusted under 35 U.S.C. 154(b) by 0 days.

(21) Appl. No.: 10/259,077

(22) Filed: Sep. 27, 2002

(65) Prior Publication Data
US 2004/0063083 A1 Apr. 1, 2004

(51) Int. Cl.$^7$ .............................. G09B 9/00; A63B 69/00
(52) U.S. Cl. ...................... 434/247; 434/236; 434/262; 434/362; 463/1; 463/7; 705/2
(58) Field of Search ........................ 434/118, 236–238, 434/247, 258, 262, 307 R, 365, 237, 308; 463/1, 7; 128/897, 898; 600/300, 316, 323, 523, 544, 545; 345/419; 705/2; 710/18

(56) References Cited

U.S. PATENT DOCUMENTS

| 5,673,691 A | * | 10/1997 | Abrams et al. ............. 600/300 |
| 5,678,571 A | * | 10/1997 | Brown ....................... 128/898 |
| 5,722,418 A | * | 3/1998 | Bro ............................ 600/545 |
| 5,730,654 A | * | 3/1998 | Brown .......................... 463/1 |
| 5,736,986 A | * | 4/1998 | Sever, Jr. .................... 345/419 |
| 5,828,943 A | * | 10/1998 | Brown ........................ 434/258 |
| 5,833,466 A | * | 11/1998 | Borg ........................... 434/236 |
| 5,876,351 A | * | 3/1999 | Rohde ......................... 600/523 |
| 5,879,163 A | * | 3/1999 | Brown et al. ............... 434/236 |
| 5,913,310 A | * | 6/1999 | Brown ........................ 128/897 |
| 5,940,801 A | * | 8/1999 | Brown .......................... 705/2 |
| 5,951,300 A | * | 9/1999 | Brown ........................ 434/236 |
| 5,974,262 A | * | 10/1999 | Fuller et al. .................. 710/18 |
| 6,057,846 A | * | 5/2000 | Sever, Jr. .................... 345/419 |
| 6,164,973 A | * | 12/2000 | Macri et al. ................ 434/247 |
| 6,206,702 B1 | * | 3/2001 | Hayden et al. ............. 434/236 |
| 6,223,074 B1 | * | 4/2001 | Granger ...................... 600/544 |
| 6,662,032 B1 | * | 12/2003 | Gavish et al. .............. 600/323 |
| 2003/0050537 A1 | * | 3/2003 | Wessel ......................... 600/300 |
| 2003/0149344 A1 | * | 8/2003 | Nizan .......................... 600/300 |
| 2003/0208113 A1 | * | 11/2003 | Mault et al. ................ 600/316 |

* cited by examiner

Primary Examiner—Joe H. Cheng
(74) Attorney, Agent, or Firm—Jensen & Puntigam, P.S.

(57) ABSTRACT

The video game includes a monitor for visual representation of a selected portion of a player's body affected by a medical condition. The information concerning the medical condition, including both its cause and effects on the body, is stored, as is a set of treatment actions for combating said medical condition, including medical treatment actions, immune system responses and spiritual actions. Also stored is the known effect of the treatment actions on the medical condition. A computer program permits the player to select and use the available treatment actions against the disease, all of which are visually produced by the program.

20 Claims, 5 Drawing Sheets

CANCER: (42) (44) (46) (48)

| VARIABLE CATEGORY | VARIABLE NAME | USER IDENTITY ACTION | RESULT OF ACTION |
|---|---|---|---|
| USER IDENTITY | AGE | CHOOSE AGE | CHANGES LOOK OF BODY |
|  | SEX | CHOOSE SEX |  |
|  | RACE | CHOOSE RACE |  |
|  | GROSS SYMPTOMS | CHOOSE TEMP, CANCER LOCATION, TUMOR TYPE AND SIZE. | CHANGES REPRESENTATION OF TUMOR. |
| CONSCIOUS ACTIVITY | TAKE MEDICINE | TAKE MEDICINE (TOPICAL, ORAL, OR INJECTED | ACTION ACCORDING TO SCIENTIFIC RESEARCH. |
|  | RADIATION | TAKE RADIATION TREATMENTS. | ACTION ACCORDING TO SCIENTIFIC RESEARCH. |
|  | CHEMOTHERAPY | TAKE CHEMOTHERAPY TREATMENTS. | ACTION ACCORDING TO SCIENTIFIC RESEARCH. |
|  | TOPICAL MEDICINE | APPLY OINTMENT |  |
|  | SURGERY | TUMOR CAN BE REMOVED. | SIMULATES EFFECTS OF SURGERY. |
|  | EAT | CHOOSE GOOD FOODS. | BOOSTS IMMUNE SYSTEM, KEEPS WEIGHT UP. |
| SUBCONSCIOUS ACTIVITY | STRESS | REACT TO STRESSES OR NOT. | MORE STRESS REACTION DECREASES TREATMENT EFFECTIVENESS. |
|  | REST | SLEEP WHEN APPROPRIATE. | BOOSTS IMMUNE SYSTEM. |
| SUB-SUBCONSCIOUS ACTIVITY (IMMUNE SYSTEM) | ENDOCRINE | CAUSE MORE IMMUNITY IN BODY. | RELEASE HORMONES TO STIMULATE IMMUNE SYSTEM |
|  | IMMUNE ACTIVITY | MATCH UP IMMUNE AGENTS WITH VIRUSES. | DISEASE HEALS FASTER. |
|  | REDUCE INFLAMMATION | CAUSE STEROIDS TO BE GENERATED AND MOVE TO INJURY SITE. | REDUCE SWELLING, INCREASES CIRCULATION AND HEALING |
|  | LYMPH FLOW | INCREASE THE FLOW OF LYMPH THROUGHOUT THE BODY | INCREASED IMMUNE RESPONSE. |
|  | TUMOR BLOOD SUPPLY. | DECREASE BLOOD SUPPLY TO TUMORS. | TUMOR SHRINKS OR DIES. |
| SPIRITUAL ACTIVITY | SYMPTOM PRAYER | PRAY FOR RELIEF OF SYMPTOMS. | WORKS SOMETIMES. |
|  | ATTITUDE PRAYER | PRAY FOR ACCEPTANCE OF THE FUTURE | RELIEF OF STRESS RELATED SYMPTOMS. |
| GOAL | LEAVE ON VACATION |  | BEING HEALTHY ON A VACATION, LIVING LONG ENOUGH TO GO ON VACATION. |
|  | KILLING TUMOR |  | GOING INTO REMISSION |

ACNE:

| VARIABLE CATEGORY | VARIABLE NAME | USER IDENTITY ACTION | RESULT OF ACTION |
|---|---|---|---|
| USER IDENTITY | AGE | CHOOSE AGE | CHANGES LOOK OF BODY |
| | SEX | CHOOSE SEX | CHANGES LOOK OF BODY |
| | ETHNICITY | CHOOSE ETHNICITY | CHANGES LOOK OF BODY |
| | ACTIVITY LEVEL | CHOOSE ACTION GAME OR THOUGHTFUL, CONTROLLED GAME. | CHANGES GAME PACE AND ACTIONS OF UI. |
| ENVIRONMENT | | CHOOSE HIGH SCHOOL OR COLLEGE | CHANGES ENVIRONMENT |
| CONSCIOUS ACTIVITY | WASHING | CAN WASH FACE AS OFTEN AS THEY WISH. | NOT ENOUGH: OILY SKIN. TOO MUCH: DRY SKIN. |
| | EATING | GREASY FOODS | OILY SKIN |
| | | HEALTHY FOODS | DRIER SKIN |
| | TOPICAL MEDICINE | APPLY SALVE | CLEARS SKIN (TOO OFTEN DRIES SKIN OUT) |
| | ORAL MEDICINE | TAKE MEDICATION | CLEARS SKIN (TOO OFTEN PUTS UI IN HOSPITAL) |
| | SCABS | CAN PICK SCABS | GETS IMPETIGO |
| | PIMPLES | CAN BREAK PIMPLES. | LOOKS BETTER FOR ONE DAY, THEN GETS A SORE FOR TWO DAYS. |
| SUBCONSCIOUS ACTIVITY | STRESS | REACT TO STRESS OR NOT. | MORE STRESS REACTION GIVES MORE PIMPLES |
| SUB-SUBCONSCIOUS ACTIVITY | ENDOCRINE | CAUSE MORE IMMUNITY IN BODY | |
| SPIRITUAL ACTIVITY | PRAY FOR RELIEF | | |
| GOAL | PROM DATE | TRY TO LOOK GOOD FOR MEETINGS. | BE KING OR QUEEN OF THE PROM |

FLU:

| VARIABLE CATEGORY | VARIABLE NAME | USER IDENTITY ACTION | RESULT OF ACTION |
|---|---|---|---|
| USER IDENTITY | AGE | CHOOSE AGE | CHANGES LOOK OF BODY |
| CONSCIOUS ACTIVITY | NOSE BLOWING | BLOW HARD | NOSE DRAINS BETTER, BUT INFECTION GOES DEEPER, POTENTIAL FOR EAR INFECTIONS. |
| | | BLOW SOFT | NEED TO BLOW MORE OFTEN, BUT INFECTION IS NOT AS SEVERE |
| | FLUSH | FLUSH SINUS WITH SALINE SOLUTION | CLEAR PASSAGES, REDUCE VIRAL LOAD. |
| | EATING | CHOOSE HEALTHY FOODS | INFECTION CLEARS SOONER. |
| | TOPICAL MEDICINE | APPLY SALVE | NOSE DOES NOT TURN RED. |
| | ORAL MEDICINE | TAKE MEDICATION | DRAINAGE CLEARS BETTER |
| | SHOT | GET A VACCINATION | INFECTION DOESN'T HAPPEN. |
| | EAT | CHOOSE GOOD FOODS. | BOOSTS IMMUNE SYSTEM |
| | VAPORIZE | USE MIST VAPORIZER. | MUCUS DRAINS BETTER. |
| SUBCONSCIOUS ACTIVITY | STRESS | REACT TO STRESSES OR NOT. | |
| | REST | SLEEP WHEN APPROPRIATE. | BOOSTS IMMUNE SYSTEM. |
| SUB-SUBCONSCIOUS ACTIVITY | ENDOCRINE | CAUSE MORE IMMUNITY IN BODY. | RELEASE HORMONES TO STIMULATE IMMUNE SYSTEM |
| | MUCUS | MAKE MORE CLEAR MUCUS. | FLUSH VIRUSES FROM NASAL PASSAGES. |
| | MUCUS IMMUNITY | ADD WHITE BLOOD CELLS TO MUCUS | WHITE BLOOD CELLS ATTACH TO VIRUS AND IMMOBILIZE THEM. |
| | INFLAMMATION | REDUCE INFLAMMATION IN MUCUS MEMBRANES | MUCUS FLOWS BETTER |
| | IMMUNE ACTIVITY | MATCH UP IMMUNE AGENTS WITH VIRUSES | DISEASE HEALS FASTER |
| SPIRITUAL ACTIVITY | SYMPTOM PRAYER | PRAY FOR RELIEF OF SYMPTOMS. | WORKS SOMETIMES. |
| | ATTITUDE PRAYER | PRAY FOR ACCEPTANCE OF THE FUTURE | RELIEF OF STRESS RELATED SYMPTOMS. |
| GOAL | LEAVE ON VACATION | | NOT HAVE TO FLY IN AN AIRPLANE WHILE SICK |
| | RELIEF | | LESSENING OF SYMPTOMS |
| | CURE | | SYMPTOMS GONE VIRAL IMMUNITY |

Columns 70, 72, 74 point to VARIABLE NAME, USER IDENTITY ACTION, and RESULT OF ACTION respectively.

ANKLE INJURY:

| VARIABLE CATEGORY | VARIABLE NAME | USER IDENTITY ACTION | RESULT OF ACTION |
|---|---|---|---|
| USER IDENTITY | AGE | CHOOSE AGE | CHANGES LOOK OF BODY |
| | SEX | CHOOSE SEX | |
| | RACE | CHOOSE RACE | |
| CONSCIOUS ACTIVITY | WALK | WALK ON ANKLE | EARLY: MORE DAMAGE, LATE: KEEPS SCAR TISSUE FROM FORMING. |
| | STRETCH | STRETCH ANKLE | KEEP SCAR TISSUE FROM FORMING. |
| | STRENGTH | EXERCISE | STRENGTHENS SUPPORTING MUSCLES |
| | TOPICAL MEDICINE | APPLY OINTMENT | |
| | ORAL MEDICINE | TAKE MEDICATION | ANKLE HURTS LESS, MORE LIKELY TO RE-INJURE. |
| | CORTISONE SHOT. | GET A SHOT INTO JOINT | INFLAMMATION GOES DOWN, MORE LIKELY TO RE-INJURE |
| | EAT | CHOOSE GOOD FOODS. | BOOSTS IMMUNE SYSTEM |
| SUBCONSCIOUS ACTIVITY | STRESS | REACT TO STRESSES OR NOT. | MORE STRESS REACTION GIVES MORE ZITS. |
| | REST | SLEEP WHEN APPROPRIATE. | BOOSTS IMMUNE SYSTEM |
| SUB-SUBCONSCIOUS ACTIVITY | ENDOCRINE | CAUSE MORE IMMUNITY IN BODY. | RELEASE HORMONES TO STIMULATE IMMUNE SYSTEM |
| | IMMUNE ACTIVITY | MATCH UP IMMUNE AGENTS WITH VIRUSES | DISEASE HEALS FASTER |
| | REDUCE INFLAMMATION. | CAUSE STEROIDS TO BE GENERATED AND MOVE TO INJURY SITE. | REDUCE SWELLING. INCREASES CIRCULATION AND HEALING |
| SPIRITUAL ACTIVITY | SYMPTOM PRAYER | PRAY FOR RELIEF OF THE FUTURE. | RELIEF OF STRESS RELATED SYMPTOMS |
| | ATTITUDE PRAYER | PRAY FOR ACCEPTANCE OF THE FUTURE | RELIEF OF STRESS RELATED SYMPTOMS. |
| GOAL | LEAVE ON VACATION | | NOT HAVE TO FLY IN A AIRPLANE WHILE SICK |

VIDEO GAME FOR ASSISTING HEALING OF THE HUMAN BODY

TECHNICAL FIELD

This invention relates generally to video games, and more specifically concerns a video game which is directed to the representation of specific treatable medical conditions of a player's body and specific treatment actions which can be used against those conditions.

BACKGROUND OF THE INVENTION

It is well know that the effect of conventional medical treatment for various bodily diseases and injuries can be enhanced by both the body's own immune system and the mental/emotional attitude of the patient. Conventional medical treatment includes prescribed medications, but may also include other treatment regimens, including for example, surgery, various forms of physical therapy, diet, exercise, and bed rest. Examples of diseases extend from the very common, such as colds, flu, or other common medical conditions, such as acne, to serious, even life-threatening diseases/conditions, such as cancer, heart disease, kidney disease, etc.

Apart from the importance of a good mental attitude to enhance conventional treatment, there are relatively few tools or techniques that the patient himself/herself can use to aid in the healing process, apart from following the advice of their physician. There are some computer-based systems which provide helpful information concerning treatment and/or rehabilitation of the body. U.S. Pat. No. 5,833,466 to Brog and U.S. Pat. No. 5,673,691 to Abrams, et al, teach modification of behavioral responses, or assisting in developing acceptable behavior traits. U.S. Pat. Nos. 5,828,943, 5,940,801 and 5,951,300, all to Brown, concern assessment of various psychological conditions. U.S. Pat. No. 6,164,973 to Macri provides information on enhancing cognitive and/or motor skills. In addition, there are some patents (U.S. Pat. Nos. 5,736,986 and 6,057,846, both to Sever, Jr.) which are directed toward the use of mental visualization to produce certain training effects, but are also indicated to be useful in treating depression and certain other undesirable conditions.

However, none of these patents are directed toward using actual medical information, in the context of a video game, to provide the player an opportunity to enhance the treatment of disease in his/her own body. Applicant's system uses a video game format, with actual scientific information concerning various diseases and treatments thereof, to enhance the healing effect of the treatments.

SUMMARY OF THE INVENTION

Accordingly, the present invention is a video game for treatment of medical conditions of a human player's body, wherein the medical conditions include but are not limited to disease, injury and/or other medical conditions. The video game comprises: a stored video program providing a visual representation of the player's body including a portion of the player's body affected by a medical condition; a memory device for storing or receiving, under program control, information concerning the medical condition to be treated, including the effect of the medical condition on said portion of the body; a memory for storing or receiving a set of treatment actions for combating said medical condition, in order to bring healing action to the body; a memory for storing or receiving known results of treatment actions on the medical condition and a stored program wherein the stored program permits a player to use said treatment actions in response to the medical condition and the effects thereof, to provide a visual representation of the effects of the treatment actions on the medical condition in accordance with said known results.

BRIEF DESCRIPTION OF THE DRAWINGS

FIG. 3 is a table showing the video game treatment information for a cancer condition.

FIG. 5 is a table showing the video game treatment information for a flu condition.

BEST MODE FOR CARRYING OUT THE INVENTION

Figure 1:
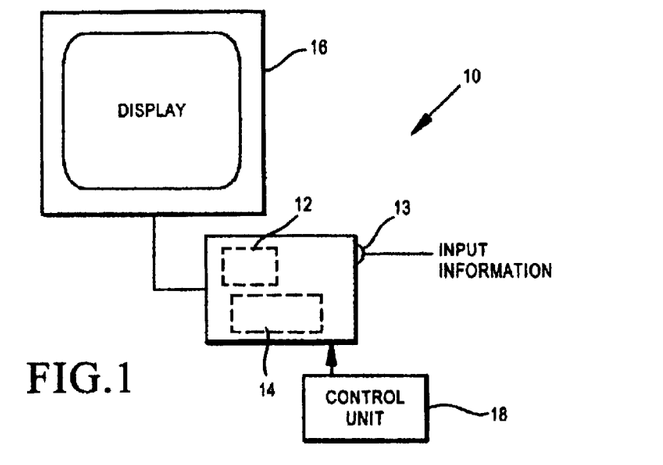
FIG. 1 is a simplified schematic view of the overall video system of the present invention.

The present invention is a video game which enhances or facilitates the healing of various medical conditions, both disease and injury, which may be present in the body of the player. Referring to FIG. 1, the video game system, shown generally at 10, includes a system memory 12, which stores physiological and other information regarding specific disease(s) and their effect on the body, referred to as a first group of information. This information will typically include actual physiological causes and effects of the disease or injury, including specifically what happens in the various physical parts of the body affected by the disease. This can include, for example, effects on tissue, blood, the various organs of the body; indeed, every physical aspect of the body known to be affected by the disease. The specific known causes of the disease and/or specific effects thereof, such as virus infections, bacteria, tumors, blood conditions, are also included in the memory 12.

All of this information concerning a particular disease or injury is available from known medical sources, such as text books, etc. Memory 12 will have such information already stored therein for selected, common diseases. For other diseases, including rarer diseases, such as for example, meningitis, certain forms of cancer and other less common, but still treatable diseases, access to memory 12 is provided at an input port 13, so that appropriate medical information concerning such disease can be provided to memory 12. This could be done in various ways, including providing the information directly into memory, scanning the information from textbooks, or even reading the information into memory. The important criteria is that the information be as complete as possible with respect to the specific physiological causes of the disease (virus, bacteria, etc.) and the effect(s) of the disease on particular physical areas of the body.

A second group of information, which is also stored in memory 12, concerns the known or conventional treatment for each disease. This treatment information includes medications which are to be taken by the patient and perhaps other specific treatment which require trained medical effort, such as surgery, chemotherapy or physical therapy. This information includes all medical treatments which are carried out by a physician or other medical personnel.

Still other treatment actions could include special dietary programs, exercise and other actions to be performed by the patient as part of a comprehensive treatment program. Other information/guidelines in the treatment program will include additional specific actions or things to avoid. The avoidance guidelines could include, for example, alcohol, incorrect drugs, too strenuous exercise or other specific actions which the patient is to avoid.

A particular patient may also have some specialized or custom treatment for his/her particular disease, in addition to more general or orthodox treatment. This would be treatment actions which are specific to a particular patient. This additional treatment information can also be stored in memory 12 for the particular disease affecting the player of the game. The ability to store custom information for a particular player is an important aspect of the present system, although the fundamental requirement is storage/access to conventional, orthodox treatment information either in memory 12 or from another source, such as an internet source. The treatment information thus could be in memory in the apparatus, or the information could be entered when needed from disk or other storage media available to the system. Typically, the system will include the ability to either update or add to conventional medical treatment information and/or receive custom information for a particular player.

In addition to the medical condition information and the medical treatment information, memory 12 will have stored therein further information, including the human body's own innate capability of combating the disease or injury. This may include information concerning the immune system response as well as other subconscious responses of the human body against the disease. Such information is well known relative to selected diseases, but will vary from condition to condition. Still further, memory 12 will have the capability of receiving and storing information concerning the effect on the cause of the disease or other medical condition of spiritual or other non-medical actions. This will include conscious activities as prayer and/or meditation. The stored information will also include particular effects that have been observed or/are generally ascribed to the selected activity, so that the program control can produce a realistic effect on the medical condition in response to the activity. This information will be varied, but will include effects which have been in fact documented, such as the known effect of meditation and biofeedback techniques for lowering blood pressure. Typically, this information will not include wholly fanciful or undocumented effects.

The information in memory 12 concerning the treatment regimen for a selected disease/condition thus includes conventional (and perhaps non-conventional) medical treatment, the body's own response from its immune system, as well as other basically subconscious responses, and spiritual responses based on knowledge and/or information of actual, proven effectiveness. The video game is thus generally reality-based relative to treatment and its effect on a particular disease.

The video system 10 also includes a stored program control which is represented at 14 in FIG. 1. It will typically take the form of a microprocessor operating in accordance with a computer program. The controller 14 correlates the treatment information in memory 12 relative to the disease/injury or other condition which is described and detailed in memory 12, in accordance with known effects, and will produce a visual representation thereof on monitor 16'. The program controller 14 will, for instance, produce a display of any selected portion of the human body which is affected by a particular disease, typically including the display of blood vessels, tissue, organs and other physiological aspects in a selected region, and to visually portray the effect of the disease on those physical aspects of the body. The display may include a representation of the particular genesis or cause of the various effect of the disease, such as bacteria, cancer cells, viruses, etc. The representation of the body and the effects of the disease or other condition are all displayed in graphic, but generally realistic, visual form.

For instance, tumor cells and bacteria causing certain disease can be shown graphically, in some cases quite similar to how they look in reality, so as to provide a realistic portrayal of the status of the disease in the player's body. The actual physical location of the disease will also be shown. The disease can also be shown representationally, in a cartoon-like form. The program control is thus capable, with stored information from memory 12, of visually portraying the disease, typically as "the enemy", a condition to be "vanquished", similar to conventional video game action.

This program control is adapted to specifically and visually portray the disease as something that can be specifically attacked and overcome, again, similar to cartoon-like villains in a conventional video game. The program control, besides being able to display the cause and effect of a particular disease in various physical regions of the body in a dramatic visual way, also has the capability of correlating and visually showing the effect on the disease of conventional medical treatment, the body's own responses (e.g. immune response) and other treatment possibilities, such as spiritual actions. The program control 14 processes all of the stored treatment information and has the capability of appropriately visually representing the effect of each treatment aspect, relative to the specific particular disease being "attacked", i.e. the disease affecting the player of the game.

The present embodiment of the video game begins with a display of the body of the user, i.e. the player. In the embodiment shown, this initial generalized image of the body can be altered to some extent to account for age, gender and race/ethnicity of the player. It should be understood, further, that other variables concerning the image can be changed to some extent so as to more accurately and faithfully represent the actual image of the player.

At this point in the game, the player enters into the action of the video game, via a video game control unit 18, relative to a particular disease or other condition the player wishes to treat. The player can, if desired, enter information concerning the disease. Full information can be provided if it is not already in memory 12; the player can also provide additional, i.e. custom, information concerning the disease, including particular information specialized to the player. The same is true for treatment information. Full treatment information can be entered, such as from a stored source thereof, such as a disk, if that information is not already stored in memory 12. Further, additional information can be entered by the player through port 13 concerning a particular treatment/regimen relative to the particular player, if desired. The treatment information can include conventional medical treatment, immune system information and other subconscious information, as well as spiritual and other internal treatment information.

Although, typically, the video game will be played with a representation of the human body, with various treatment resources, the game can use a representation of the player himself/herself as an active agent (hero) in the game, to carry out a particular treatment task, with a particular treatment tool. This could include, for instance, representations of activity of the player (agent) internally of the body, such as in the use of a decongestant spray, for instance. More typically, however, the "player" will be outside of the body, directing (choosing) the various treatment regimens and tools against the disease.

By observing the effect of the various treatment tools on the disease, particularly those which are actually being used/followed by the player on his/her own body, the player is reinforced as to the effect of the treatment, i.e. the effect of the treatment on the player's own body is reinforced and strengthened by observing visually the realistic effect of the treatment on the video game virtual body. The player is thus engaged actively in training of his/her body relative to the effect of the treatment by means of the video game. This coincides with the positive effects of visualization in other areas, such as athletic achievement. The player thus aids or enhances the effect of his/her own treatment through visualizing its effect on the body image on the monitor.

The video game control panel has a map of the body, which shows the various trouble spots in the body for the particular disease, which is based on actual information obtained from the player, in addition to conventional information. Certain conditions concerning the body can be provided by the player, such as the present level of relevant chemicals and treatment agents already present in the body. With the control panel, the player can select a particular area of the body, which will then result in the program control focusing on that portion of the body. The monitor will then show that particular portion, such as a particular blood vessel, such as a cardiac vessel, organ tissue or some other part of the body. The effect of the various treatment regimens is then visually demonstrated on that portion of the body, such as the effect of particular medications/chemicals, as well as immune system responses and spiritual actions.

The player has the opportunity to select particular treatment agents according to his/her overall actual treatment plan, so that the treatment agents in the game basically mimic the actual treatment on the player's body. This will include, as indicated above, conventional medical treatment, as well as immune system responses and selected spiritual actions, such as prayer and meditation. As the player selects the treatment tools and uses them in the game, like various tools or weapons in a conventional action video game, the effects of such treatment tools on a particular disease is presented visually on the monitor, by the program control, and is thus seen by the player. This visualization of the effects of the treatment tools on the disease provides the desired "training effect" in the player's body, i.e. it enhances or strengthens the effect of the treatments.

For instance, treatment of a disease may require the use of certain prescribed medications, a particular diet, bed rest, etc. Certain immune responses to the disease will also occur naturally, and will be taken into account. Further, the player may elect to use certain spiritual actions. The player will actually carry out the conscious treatment actions for his/her disease, such as taking prescribed medications. The video game, showing the same disease and treatment, will show the positive effects of the treatment on the disease. This aids the player in visualizing a positive effect of the treatment, providing the desired training effect on the player's body. The video game will provide an accurate visual representation of selected treatments on the disease and will conclude with a successful resolution of the condition; the video game then ends.

Figure 2:
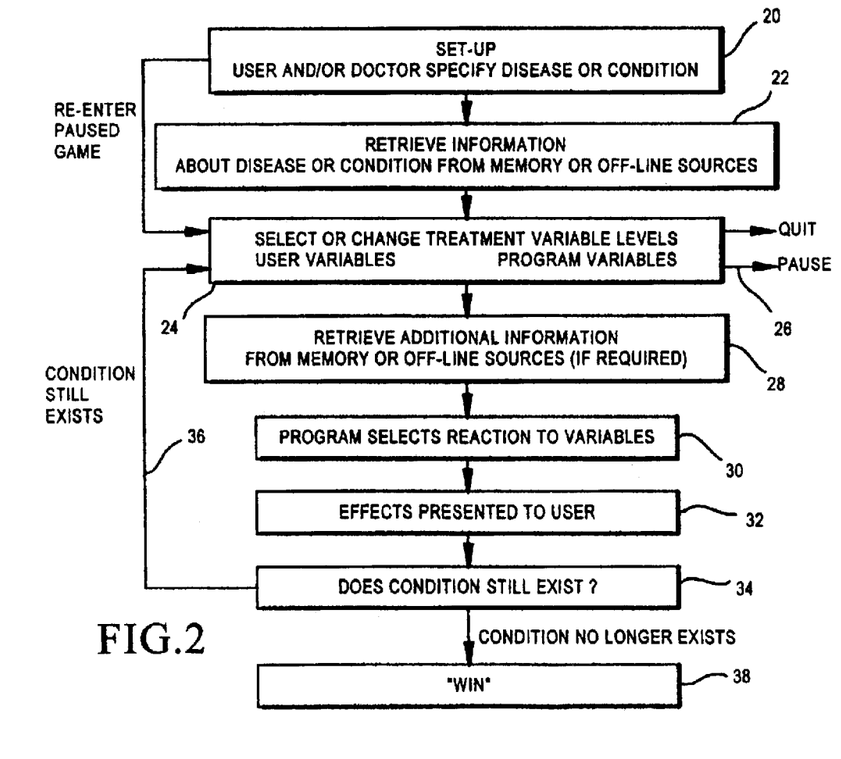
FIG. 2 is a generalized flow chart for the video game of the present invention.

FIG. 2 is a flow chart for the control program of the present invention in accordance with the above description. The flow chart is not specific to any particular disease or treatment, but is used generically. Initially, as shown in block 20, the player and/or the doctor first specifies the particular disease or condition affecting the player to be the subject of the game. In block 22, information concerning the particular disease is either retrieved from existing memory in the apparatus or from other sources. In block 24, the initial treatment variables, both from the user's standpoint and for the particular disease is selected by the user. The treatment may be variable in terms of different levels of, for instance, medications, which the program itself can either specify or which can be selected by the user. At this point, the player can quit the game at 25 or the game can be paused at 26. Additional information concerning either the disease or the treatment can then be added, at block 28.

The program, at block 30, then selects the particular desired reaction of the characteristics or causes of the disease, such as bacteria, cancer cells or other causes of the disease or condition, to the treatment and/or the variable levels within the treatment. For instance, the disease may react differently to different levels of medication.

The effects selected by the program from memory 12 or other sources (at input 13) then are presented in a visual (display 16) representation to the user on the monitor. This is represented at block 32. As indicated above, the visual representation can be in various forms. The results can be medically realistic, or somewhat fanciful and cartoonish in nature, or some combination thereof. The important aspect, however, is to provide a clear visual, understandable representation of the effect of the various treatments on the disease. The visual effect will enhance the actual effect of the treatment on the body of the player as the visual representation makes a specific impact on the user.

In the next block 34, information is entered by the user or the doctor or other health professional concerning the continued existence of the disease. This can be accomplished through testing or other diagnostic procedures, similar to those which indicated the condition in the first place. If the condition still exists, shown at line 36, the program loops back to the treatment block 27, which then may be changed in accordance with actual changes in the treatment for the player. Alternatively, if the condition no longer exists, the program terminates at block 38, with a "win" condition, the condition or disease affecting the player being cured.

FIG. 3 is a table showing a first specific example relative to the video game of the present invention. This concerns a cancer condition. This example, as well as other examples described hereinafter, is for illustration and not exclusive to the video game of the present invention. FIG. 3 shows four columns: the general type of identity/activity in column 1, referred to at 42; the specific type of identity/activity in column 2, referred to at 44; the specific type of treatment action in each category of column 1, in column 3, referred to at 46; and in column 4, referred to at 48, the desired response of the body of the player to the treatment selected by the user. It should be understood that each of the columns for a particular disease, including the example of FIG. 3, are by way of illustration and are not considered to be complete for a particular disease.

In the first column of FIG. 3, the user is identified, as well as the particular disease. This includes, in column 46, the age, sex (gender) and race of the player. This will result in a change in the particular image of the player on the monitor. Column 44 includes a reading of basic or gross symptoms of the disease. The action by the user includes the specific choices concerning the variables in column 44. The results from the action in column 48 will produce particular changes in the body, as indicated above, as well as changes in the representation of the tumor.

Under the "conscious activity" heading of columns 42 and 44, specific treatments include medications, radiation, chemotherapy, surgery and diet, as examples. Columns 44 and 46 identify the general and specific actions actually taken by the user. The results of the various actions, as represented on the monitor, are set out in column 48. The subconscious activities and responses relative to the treatment of cancer include stress actions and rest, while immune system activities and responses include use/stimulation of the various appropriate immune glands and other immune system actions related to the disease. Spiritual activities for cancer treatment include prayer and meditation relative to the disease itself and the player's attitude toward the disease. The ultimate goal is to kill the tumor, while an intermediate goal may, for instance, to be able to go on a vacation.

Again, for each specific activity listed in column 44, there is an associated treatment/action in column 46 and a result in column 48. The information in all of FIG. 3 is for example only. Additional, perhaps more comprehensive, information is possible, particularly for complex, different diseases such as cancer. Such information can be provided at input 13.

Relating now the material of Table 1 and the above description of FIG. 2, the user first will provide age, gender, race and other information, including the symptoms and the location and type of tumor (column 46). The program will then load the details of the causes, manifestations and the treatments for the cancer (conscious activities in column 46), and the reaction of the cancer or symptoms to various treatments and actions (conscious activities in column 48). The program will also load how the various cancer conditions are presented visually to the user. Program variables and treatment variables are presented to the user, including activities under the conscious category, subconscious category, immune system category and spiritual category. The player, for instance, can simulate the application of certain topical medicines or oral or injected medications, radiation and chemotherapy treatments, diet and rest under the conscious or subconscious categories.

The user also can vary particular immune system variables which are not consciously controllable, such as blood flow to the tumors, lymph flow information levels, internal hormone levels, immune, system responses, stress responses and organ reaction to the disease. The program can also retrieve additional information and, in accordance with scientific knowledge and evidence, the program will determine the body's response to the treatment variables indicated above and provide a corresponding visual representation to the user (block 32 in FIG. 2).

Again, the visual representation may be either very close to a literal representation of the effect on the cancer, or it might be a more cartoonish version of the desired reaction to the treatment. Relative to blocks 34 and 48, when the medical condition is successfully resolved, the program will move to the "win" portion of the game. There may be provided some clear indication thereof, such as flashing lights, music or other indications.

Figure 4:
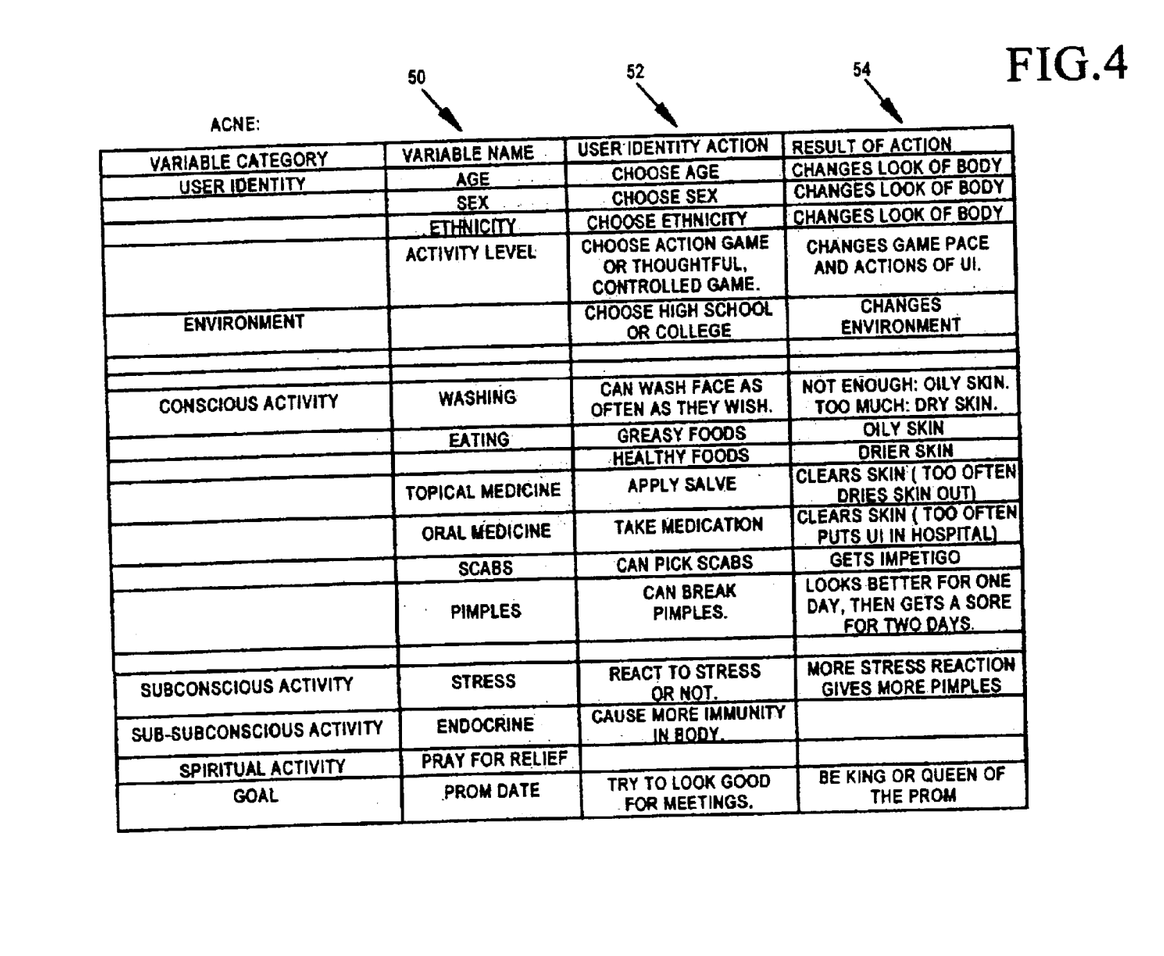
FIG. 4 is a table showing the video game treatment information for an acne condition.

FIG. 4 provides program information for the medical condition of skin acne, specifically column 50, indicating the identity of the variable, column 52 which concerns treatment possibilities and other aspects of acne, and column 54, which indicates the results of the treatment activities. Correlating FIG. 4 with FIG. 2, the player will first enter information concerning the age, gender and race of the player as well as location and type of the acne. The computer program will obtain from memory or other source details of the acne condition, including the causes and manifestations of the acne, as well as prescribed treatments and the known reactions of the acne to the various treatments, as well as possible user actions. The presentation of that information to the user will also be determined by the program.

Relative to the specific variables (block 24 in FIG. 2), the user can change or modify the program for conscious activities to simulate cleansing (washing actions), diet, the application of topical medicines, the use of selected oral medications, and specific patient actions, such as picking of the acne scabs and breaking of the acne pimples. The user can also choose to vary specific subconscious body variables, including hormone levels, stress levels, immune system variables and immune system responses. From block 30 and column 54 in FIG. 4, the program determines the response of the body to variations of the selected treatments and actions discussed above and shown in FIG. 4. The program will then present a visual simulation (block 32 in FIG. 2) to the user showing the effects of the treatments and actions, including perhaps a literal view of the acne pimples growing or shrinking or a cartoonish representation thereof, as well as perhaps both microscopic and macroscopic views of the user's skin. As the condition is significantly reduced or eliminated in accordance with preselected criteria, the program will move to the "win" conclusion (block 38 in FIG. 2) with even a somewhat fanciful or humorous desired result, such as selection for prom queen or king (as an example).

A flu condition is shown in FIG. 5, with columns 70, 72 and 74 identifying treatment and results. After inputting just the age of the player, the program will first load information about the disease (block 22 in FIG. 2) and then the known treatments, provided at column 72, referring to block 24 of FIG. 2. Examples of some treatments, in the conscious, subconscious, immune system and spiritual levels, are shown in FIG. 5, correlating to block 24 in the program. Again, these are illustrative examples and are not necessarily complete. The program will also load the specific reactions of the body to the selected treatments and the representation thereof will be presented to the user.

In column 72, note that the player can change or modify the treatment protocol in the program, including specific levels of washing, application of topical medicines, various oral or injected medications, diet and use of a vaporizer, as examples.

The player will also be able to select and vary certain immune system conditions, such as an increase in mucous production, reduction of inflammation levels and matching immune agents with viruses, among others. The program will control the times of application of the medications, as well as taking into account the normal ebb and flow of body chemicals and conditions. In block 30, the program will determine and select the body's responses to the treatment programs and the player's actions as shown in column 74 of FIG. 5. The program will prepare and present a specific visual representation (block 32 of the program) to the user showing the effects of the variations of the treatments on the flu condition. The representation could include a macroscopic as well as a microscopic view of the specific treatment actions and the body's response. A cessation of the flu will result in a "win" result (block 38).

Figure 6:
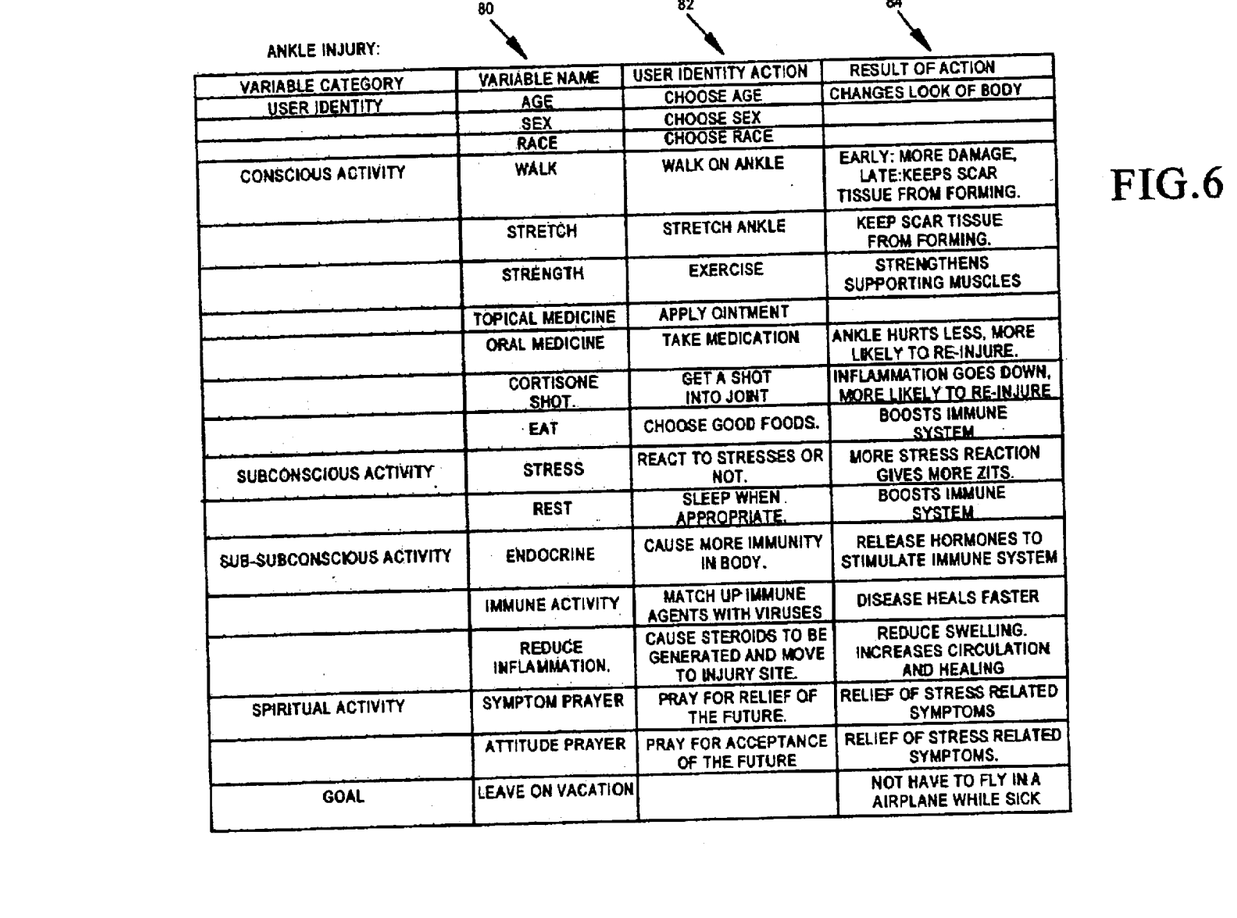
FIG. 6 is a table showing the video game treatment information for an ankle sprain condition.

FIG. 6 shows the use of the video game of the present invention for another example of a medical condition, specifically, an ankle injury. Relative to FIGS. 6 and 2, the player can input the age, race and gender into the program, as well as other information concerning injury (block 20 in FIG. 2), including body type, location and type of specific characteristics of the ankle injury. Relative to block 24 in FIG. 2 and columns 80 and 82, the program will then load the details of the specific treatments and actions which are known relative to healing the ankle injury, and will also load the known information concerning how the injury typically responds to the specific treatments (block 30 in FIG. 2 and column 84 in FIG. 6).

With respect to treatments in FIG. 6 (block 24 in FIG. 2), the user has the opportunity to select and change certain specific treatment, such as the use of topical medicines, oral or injected medications, exercise, physical therapy, diet and rest. Other treatment possibilities not shown in FIG. 6 can include surgical procedures, procedures to strengthen the joint, ligament and tendons, and antiinflammatory medications. The player can also choose certain immune system responses, such as blood flow to and from the injury site, immunity levels, general immune system response, internal steroid action to the injury site, among others. Spiritual activities can also be selected.

The known effects of the various treatments are shown realistically to the user (block 36 in FIG. 2). The visual presentation might include an accurate representation of the actual symptoms of the specific injury, i.e. the ankle injury, and how it changes relative to treatment, or it might include a cartoonish version thereof. These representations could include the macroscopic and microscopic actions which occur at the injury site. Lastly, at block 30, as the injury heals, the program will exit as a win.

The above illustrations are by way of examples only, showing the principles of the present invention, namely, the identification and treatment of actual physiological conditions of the body including disease and injury. Such a medical condition can be identified by conventional stored information which may also include specialized information relative to a specific disease or injury for a particular patient. In the videogame, the player has the ability to select and introduce particular treatment actions in response to the disease. The treatments can be stored or can be provided from an outside source. Additional treatment information can be entered into memory.

The disease and treatment information includes conventional information stored in the system, or it can be provided or supplemented from other sources, including internet sources of such information. The game can include a library of information on a wide variety of medication conditions, i.e. disease and/or injury. Negative actions, i.e. those activities to be avoided for a particular disease/injury, can also be included in the game.

The game has the result of reinforcing through visualization for the player the desired effect of various known treatments on a particular disease affecting the player. Further, it is a specific encouragement for the player to actually carry out the conscious treatment actions. The player also becomes well informed on his/her disease/injury.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A video game system for treatment of medical conditions of a human player's body, comprising:
   a first memory section for storing or receiving information concerning a medical condition to be treated, including the effect of the medical condition on a portion of the player's body affected by the medical condition;
   a second memory section for storing or receiving a set of treatment actions for combating said medical condition, to bring healing action to the player's body;
   a third memory section for storing or receiving known result/information of the treatment actions on the medical condition; and
   a stored video program and controller operating with said first, second and third memory sections, for providing a visual representation of the player's body, including said portion of the player's body affected by the medical condition; wherein the stored video program and controller permits a player to select one or more treatment actions and provides a visual representation of the effects of the selected treatment actions on the medical condition, in accordance with the known result information, to provide reinforcement of the effect of said selected treatment actions on the medical condition of the player.

2. A video game of claim 1, including means for adding additional medical condition information to the previously stored medical condition information, and for modifying the previously stored medical condition information.

3. A video game of claim 1, wherein the visual representation of the player's body includes a visual representation of the medical condition.

4. A video game of claim 3, wherein the medical condition is caused by a virus.

5. A video game of claim 3, wherein the medical condition is caused by bacteria.

6. A video game of claim 3, wherein the medical condition is cancer.

7. A video game of claim 3, wherein the medical condition is an injury.

8. A video game of claim 3, wherein the medical condition is a disease.

9. A video game of claim 1, wherein treatment action information specific to the player can be added to the stored treatment information.

10. A video game of claim 1, wherein a plurality of portions of the human body which are affected by said medical condition are represented.

11. A video game of claim 1, wherein said portion of the body includes a specific body organ.

12. A video game of claim 1, wherein said portion of the body includes a selected part of the blood circulation system.

13. A video game of claim 1, wherein said portion of the body includes a selected part of the oxygen circulation and recovery system.

14. A video game of claim 1, wherein the stored treatment actions include conventional medical treatment actions and selected medications known to be effective for said medical condition.

15. A video game of claim 1, wherein the treatment actions include immune system responses of the human body to said medical condition.

16. A video game of claim 1, wherein the treatment actions include spiritual activity.

17. A video game of claim 1, wherein the stored program permits the player to change selected physical characteristics of the visual representation to more closely match the player.

18. A video game of claim 1, wherein the medical condition information, the treatment actions therefor and the known results thereof are stored external to the video game apparatus and are available to the stored program upon request.

19. A video game of claim 1, wherein the stored program permits the player to select the portion of the player's body to be represented.

20. A video game of claim 1, wherein the visual representation is provided by a video monitor.

* * * * *